United States Patent
Kajita

(10) Patent No.: US 11,678,950 B2
(45) Date of Patent: Jun. 20, 2023

(54) MULTIPLE-VIEWPOINT VIDEO IMAGE VIEWING SYSTEM AND CAMERA SYSTEM

(71) Applicant: Hiroki Kajita, Ichikawa (JP)

(72) Inventor: Hiroki Kajita, Ichikawa (JP)

(*) Notice: Subject to any disclaimer, the term of this patent is extended or adjusted under 35 U.S.C. 154(b) by 715 days.

(21) Appl. No.: 16/643,880

(22) PCT Filed: Jun. 19, 2018

(86) PCT No.: PCT/JP2018/023191
§ 371 (c)(1),
(2) Date: Mar. 3, 2020

(87) PCT Pub. No.: WO2019/044124
PCT Pub. Date: Mar. 7, 2019

(65) Prior Publication Data
US 2020/0268471 A1 Aug. 27, 2020

(30) Foreign Application Priority Data

Sep. 4, 2017 (JP) .............................. JP2017-169185
Dec. 26, 2017 (JP) .............................. JP2017-248945

(51) Int. Cl.
*A61B 90/00* (2016.01)
*A61B 90/50* (2016.01)
(Continued)

(52) U.S. Cl.
CPC ............ *A61B 90/361* (2016.02); *A61B 90/30* (2016.02); *A61B 90/50* (2016.02); *G06V 10/141* (2022.01);
(Continued)

(58) Field of Classification Search
CPC . A61B 2090/371; A61B 90/30; A61B 90/361; A61B 90/37; A61B 90/50;
(Continued)

(56) References Cited

U.S. PATENT DOCUMENTS

2016/0165222 A1* 6/2016 Yamaoka ............. H04N 13/359
348/51
2017/0202633 A1* 7/2017 Liu ........................ G16H 40/63
(Continued)

FOREIGN PATENT DOCUMENTS

JP 2000102547 A 4/2000
JP 2012120812 A * 6/2012
(Continued)

OTHER PUBLICATIONS

Mase Kenji, Tokai Shogo, Kawamoto Tetsuya, and Fujii Toshiaki, "Study of User Interface Design of Peg Scope Navigation Method for Multi-view Image," Human Interface Society, Research Reports, vol. 11, No. 1, pp. 7-12, 10-11, Mar. 2009.

*Primary Examiner* — Mainul Hasan
(74) *Attorney, Agent, or Firm* — Renner, Kenner, Greive, Bobak, Taylor & Weber

(57) ABSTRACT

The present invention provides a multi-viewpoint video image viewing system that allows a viewer to view a multi-viewpoint video content and removes in advance video images in which hands are hidden as a video image candidate. A first invention of the present application selects video images to be displayed on a video image display section in advance and presents the selected video images to a viewer by causing an information processing apparatus to perform hand-target image recognition on motion image (video image) data that includes image data captured with a plurality of video cameras and a frame string disposed in a time region to select video images showing a hand or not to select video images showing no hand.

14 Claims, 15 Drawing Sheets

(51) Int. Cl.
  *H04N 13/282*    (2018.01)
  *A61B 90/30*     (2016.01)
  *G06V 10/25*     (2022.01)
  *G06V 10/141*    (2022.01)
  *G06V 20/40*     (2022.01)
  *G06V 40/10*     (2022.01)

(52) U.S. Cl.
  CPC .............. *G06V 10/25* (2022.01); *G06V 20/46* (2022.01); *G06V 40/107* (2022.01); *H04N 13/282* (2018.05); *A61B 2090/365* (2016.02); *A61B 2090/502* (2016.02)

(58) Field of Classification Search
  CPC .... G06V 40/107; G06V 20/46; G06V 10/141; H04N 13/282; H04N 5/23299
  See application file for complete search history.

(56) References Cited

U.S. PATENT DOCUMENTS

| | | | | |
|---|---|---|---|---|
| 2018/0055502 | A1* | 3/2018 | Charles | A61B 1/32 |
| 2019/0038362 | A1* | 2/2019 | Nash | A61B 34/25 |
| 2019/0191146 | A1* | 6/2019 | Koyama | H04N 7/18 |
| 2021/0174652 | A1* | 6/2021 | Hirasawa | G08B 13/1968 |

FOREIGN PATENT DOCUMENTS

| | | | |
|---|---|---|---|
| JP | 2013245782 A | 12/2013 | |
| WO | 2015173851 A1 | 11/2015 | |

* cited by examiner

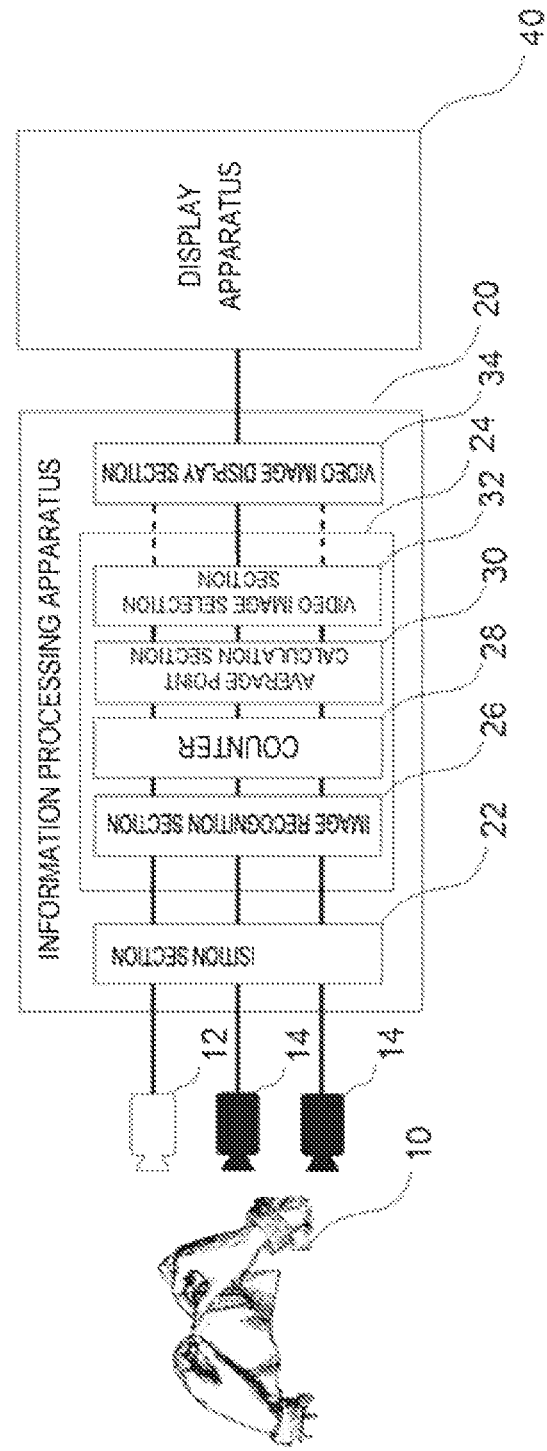
[Figure 1]

[Figure 2]
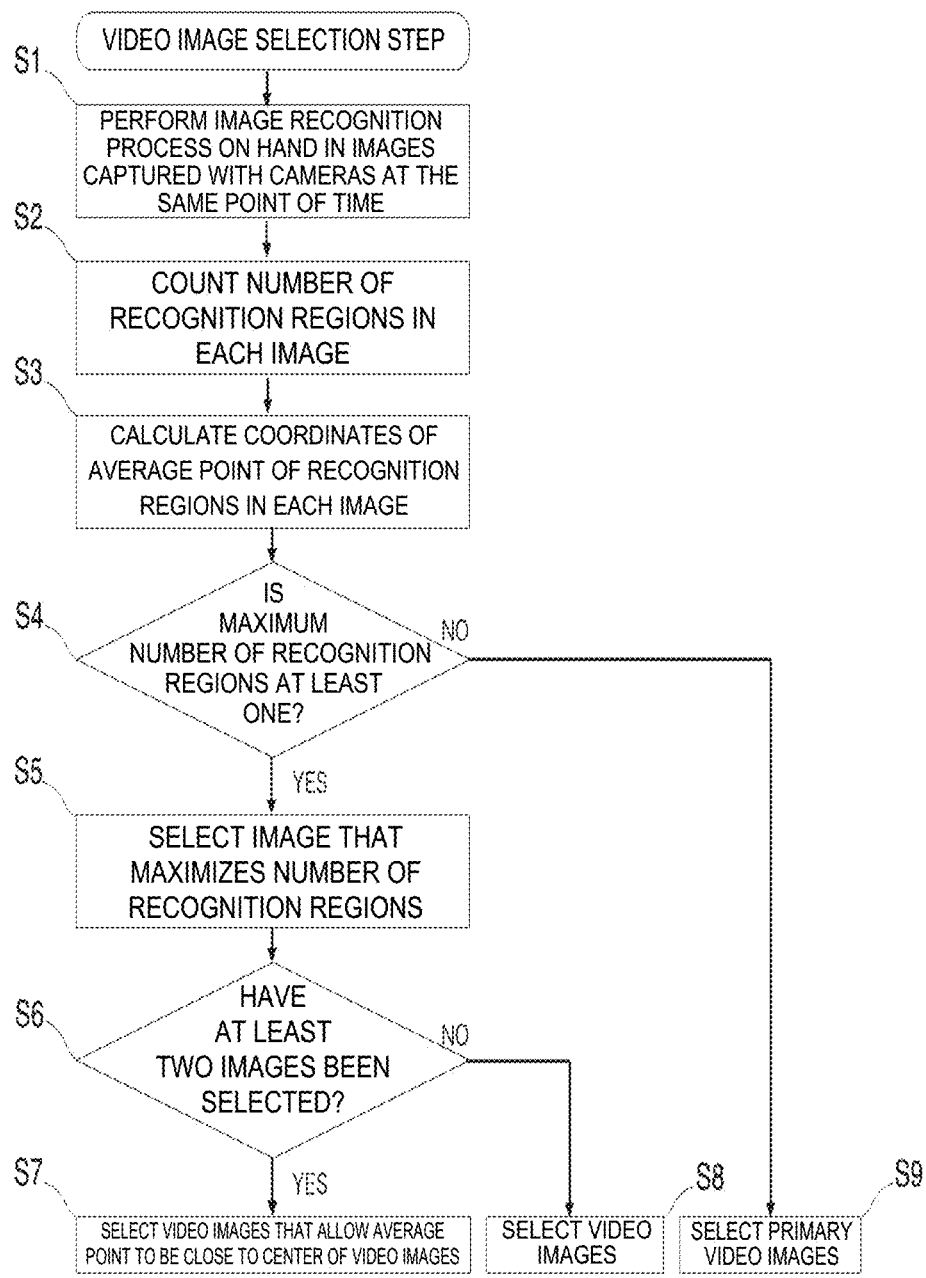

[Figure 3]
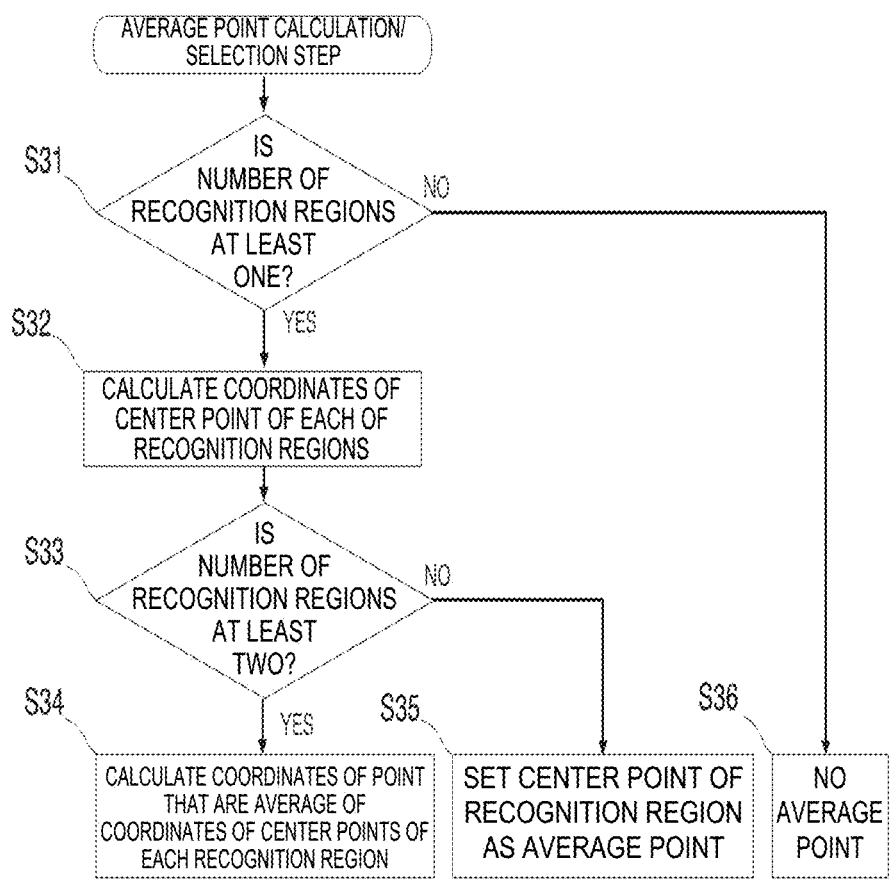

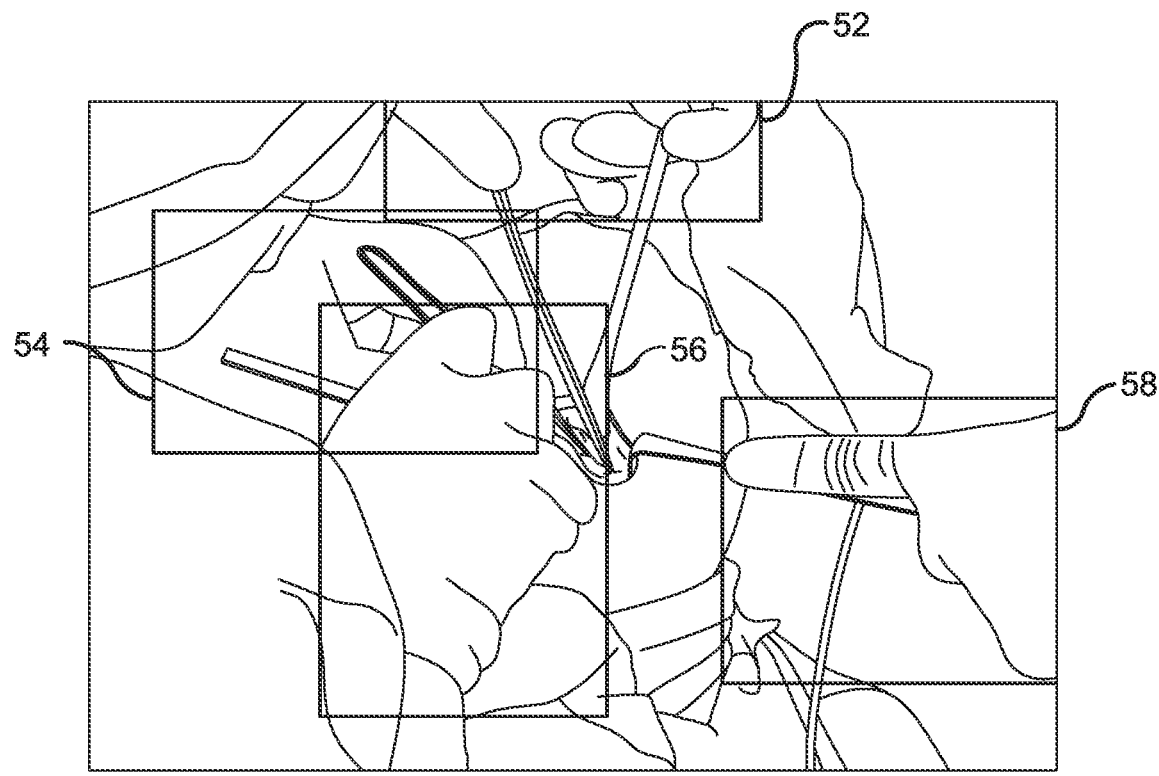
[FIGURE 4]
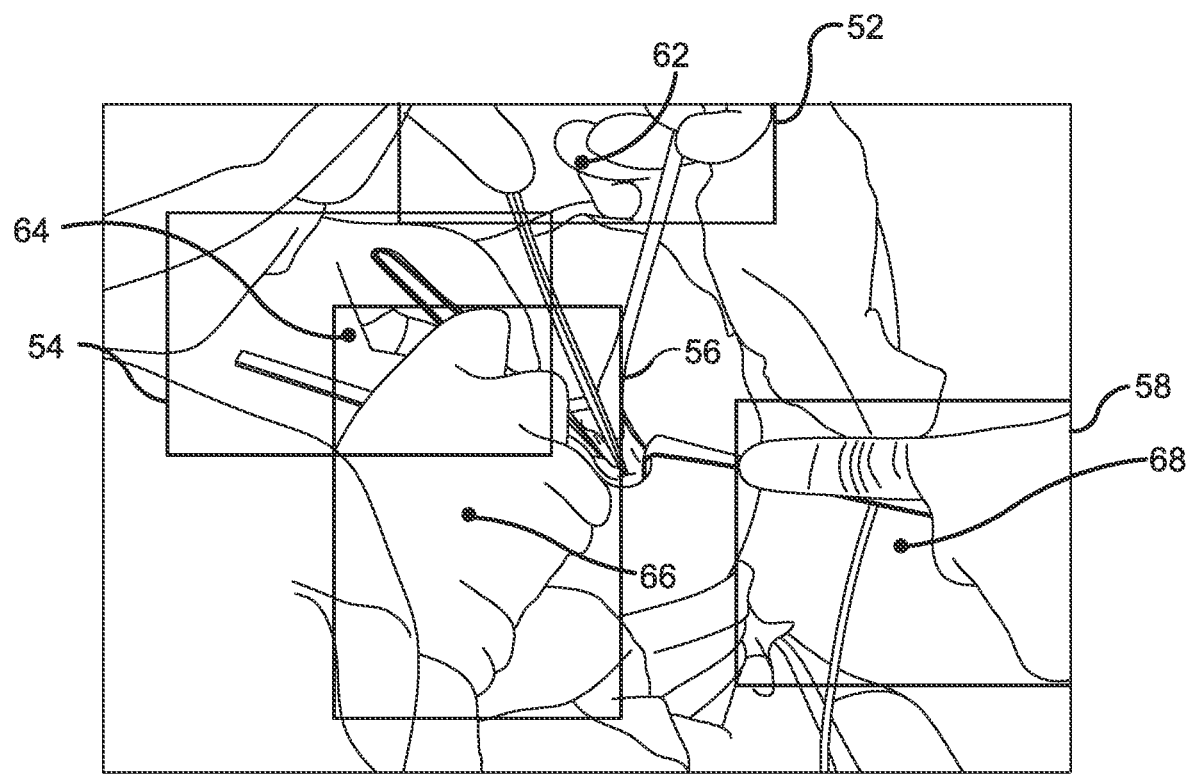
[FIGURE 5]

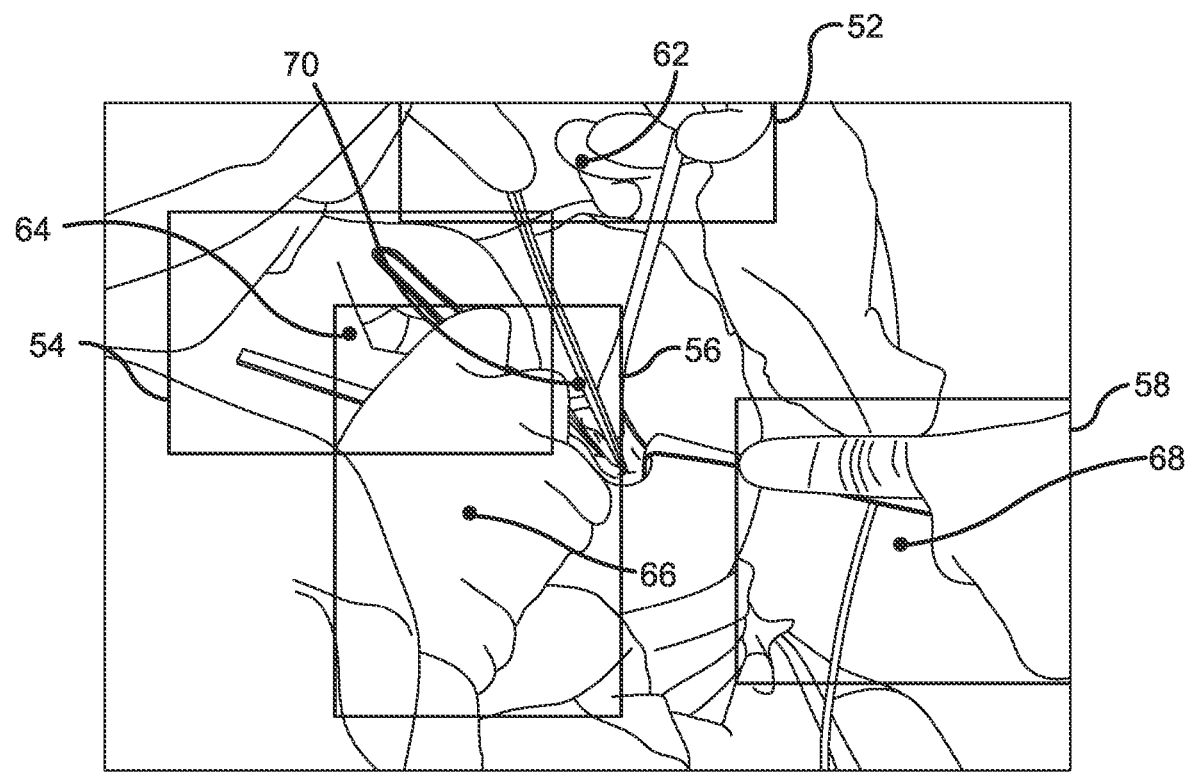
[FIGURE 6]
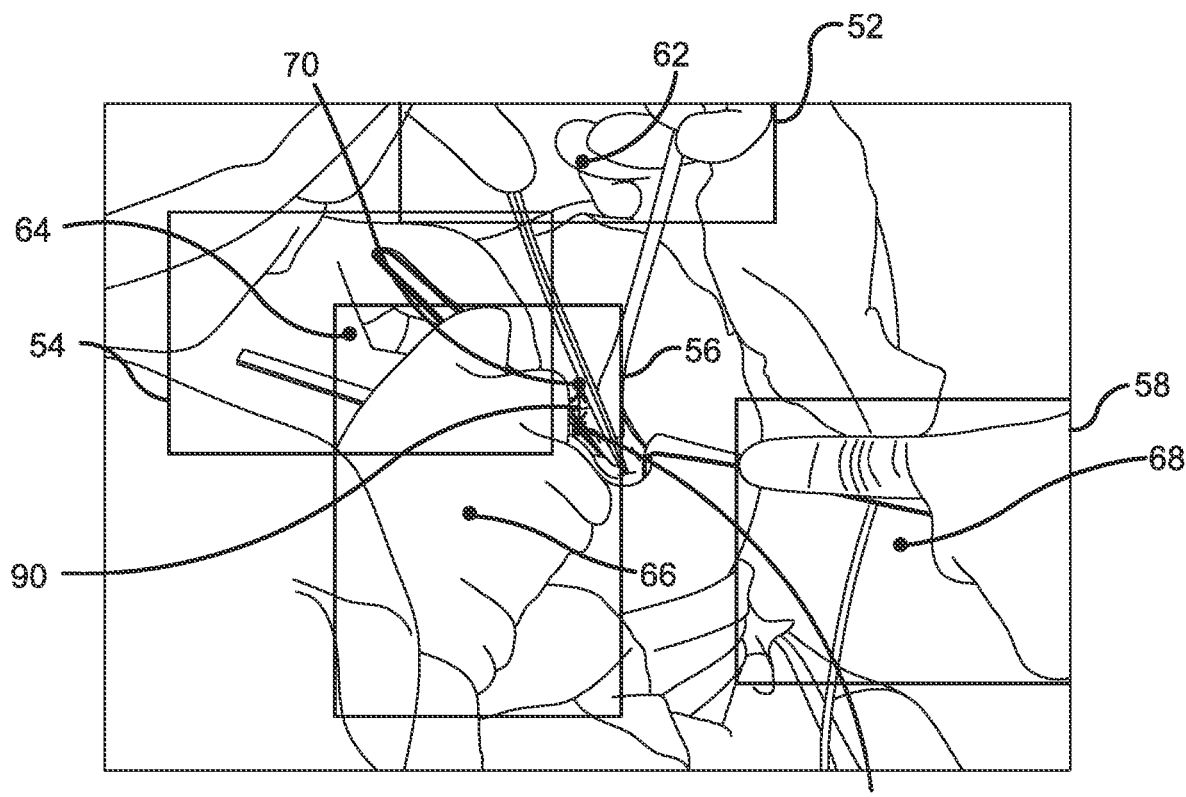
[FIGURE 7]

[Figure 8]
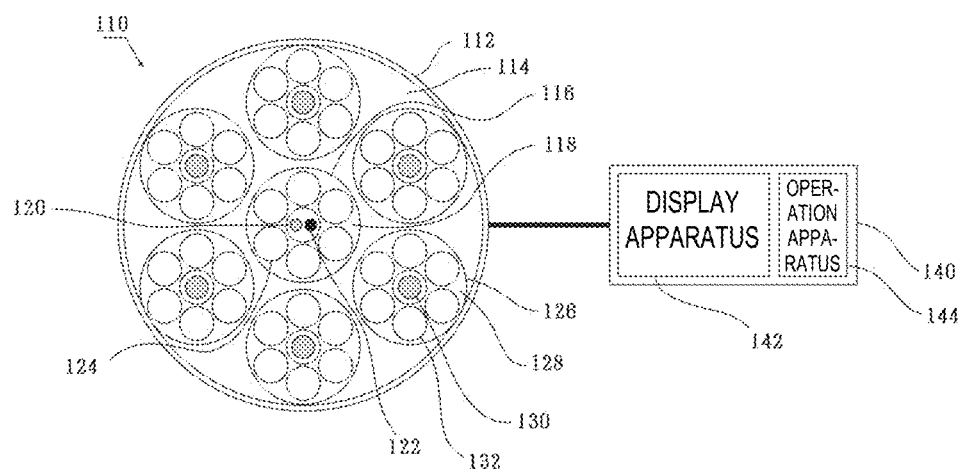
[Figure 9]
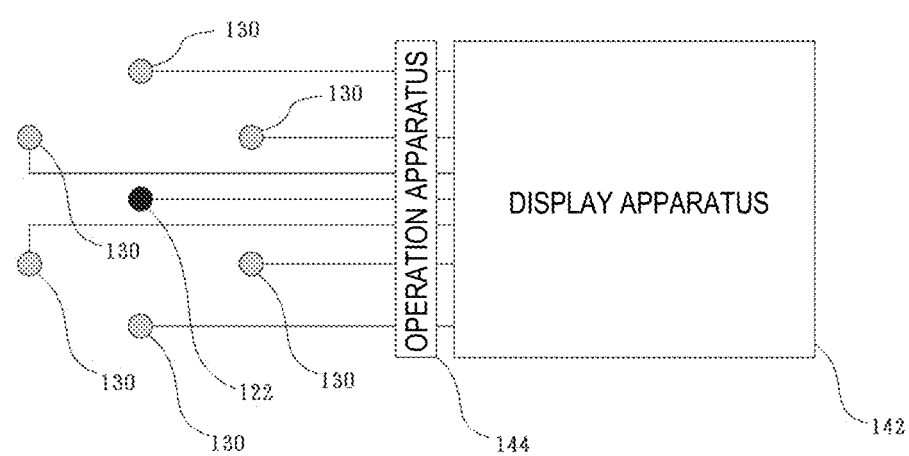

[Figure 10]
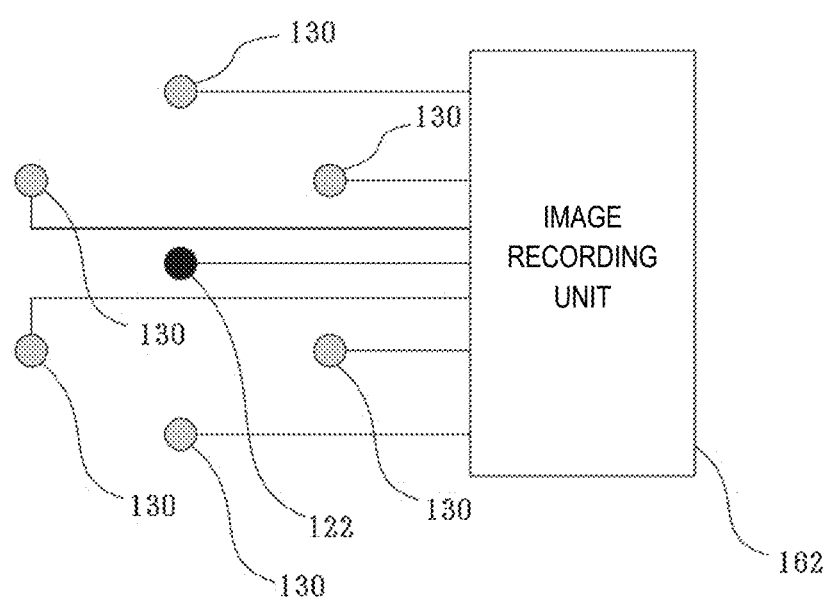

[Figure 11]
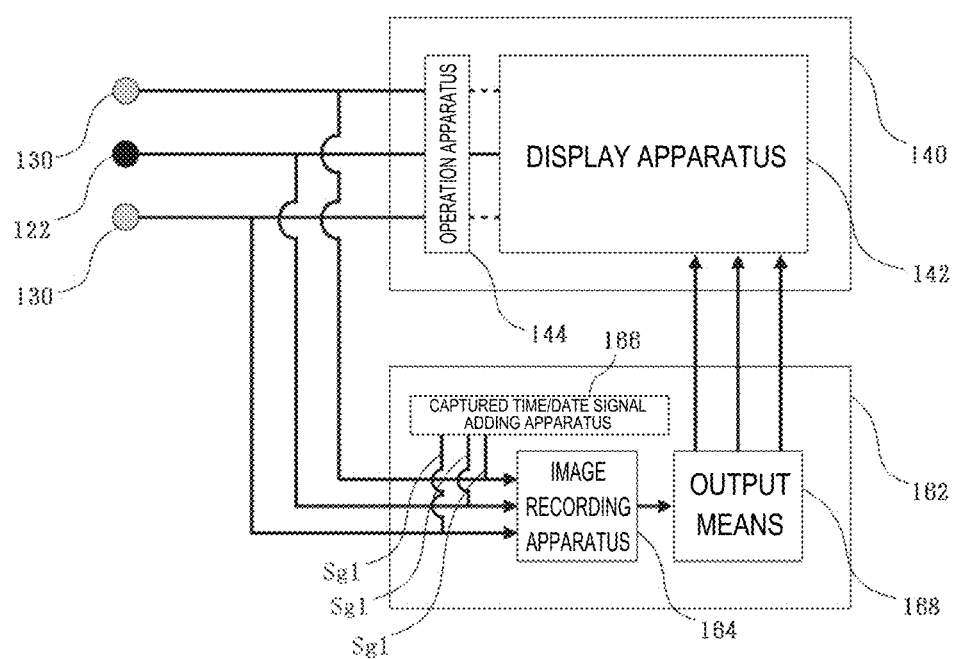

[Figure 12]
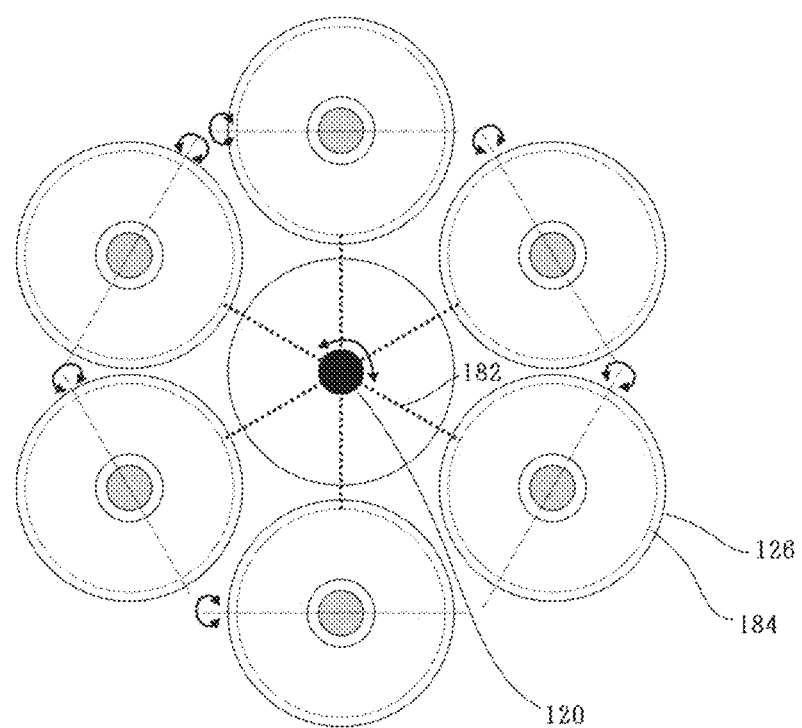

[Figure 13]
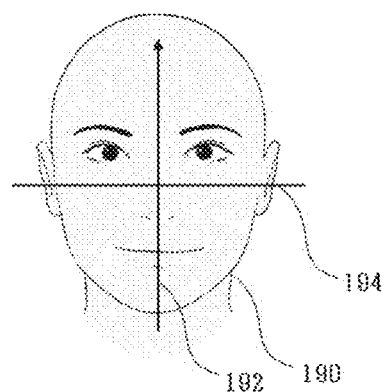
[Figure 14]
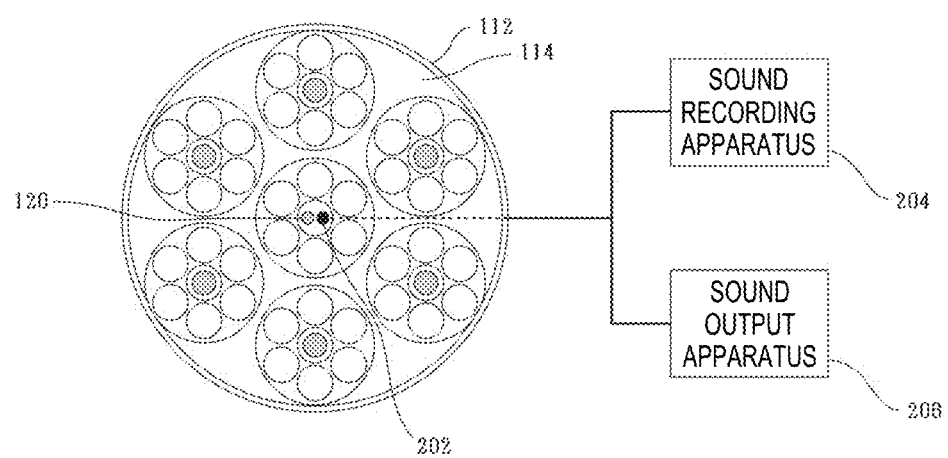

[Figure 15]
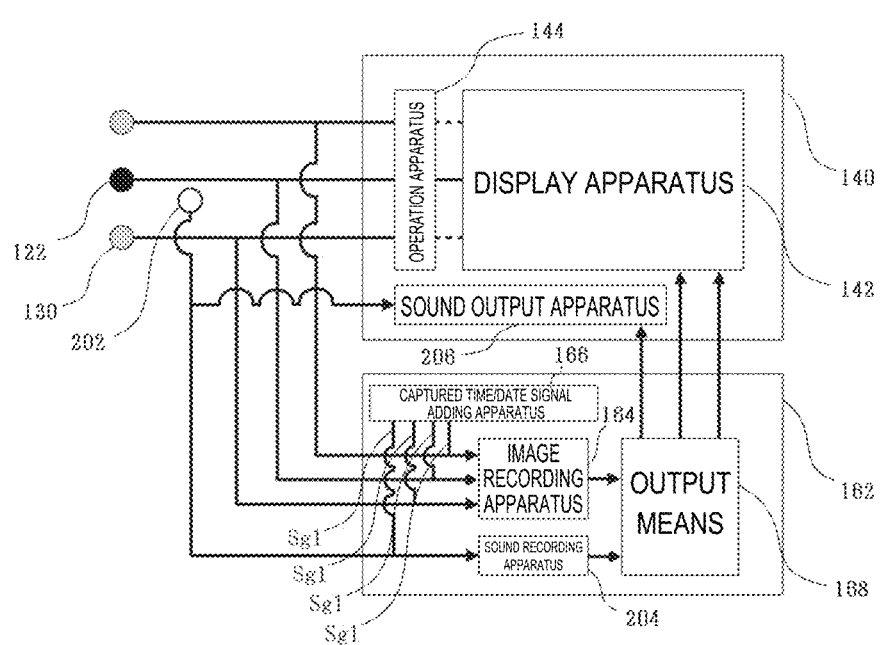

[Figure 16]
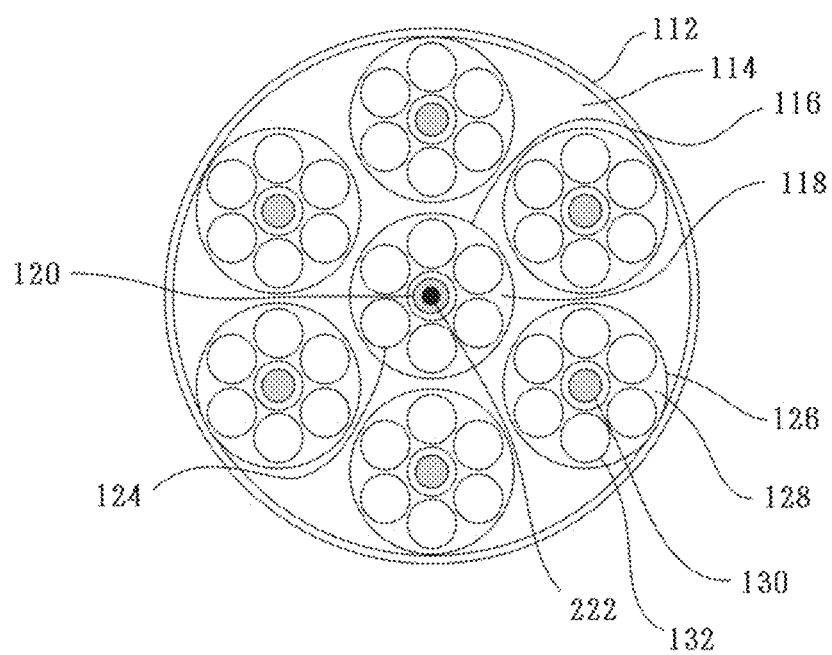

[Figure 17]
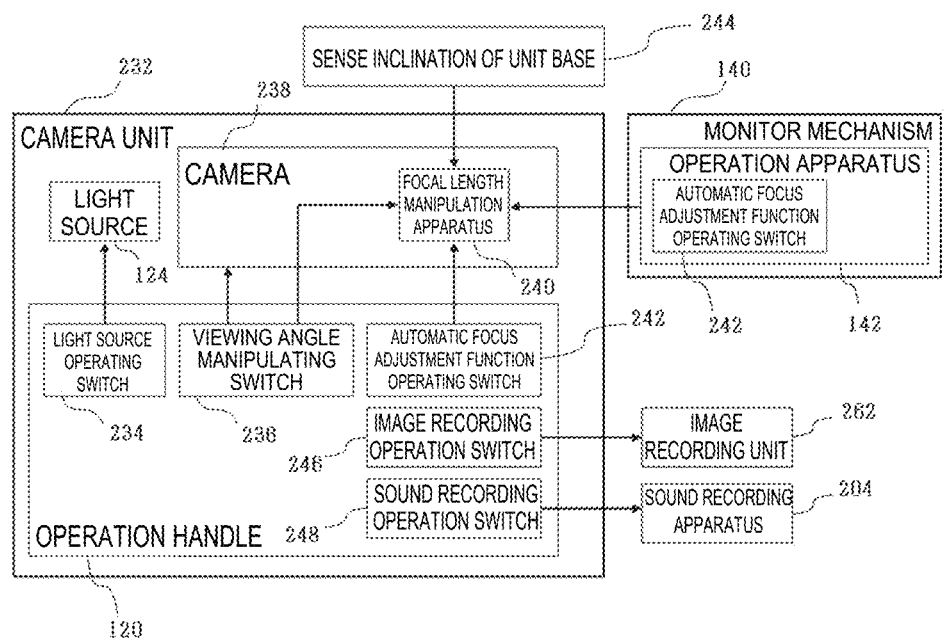
[Figure 18]
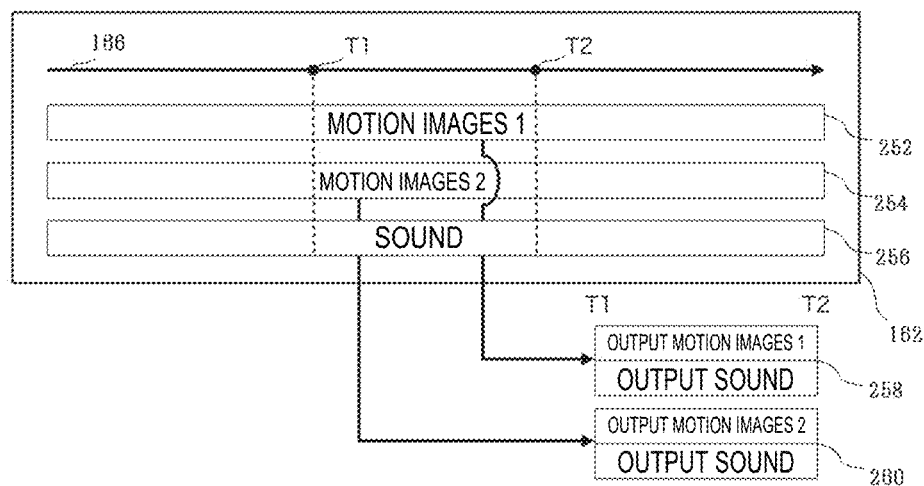

[Figure 19]
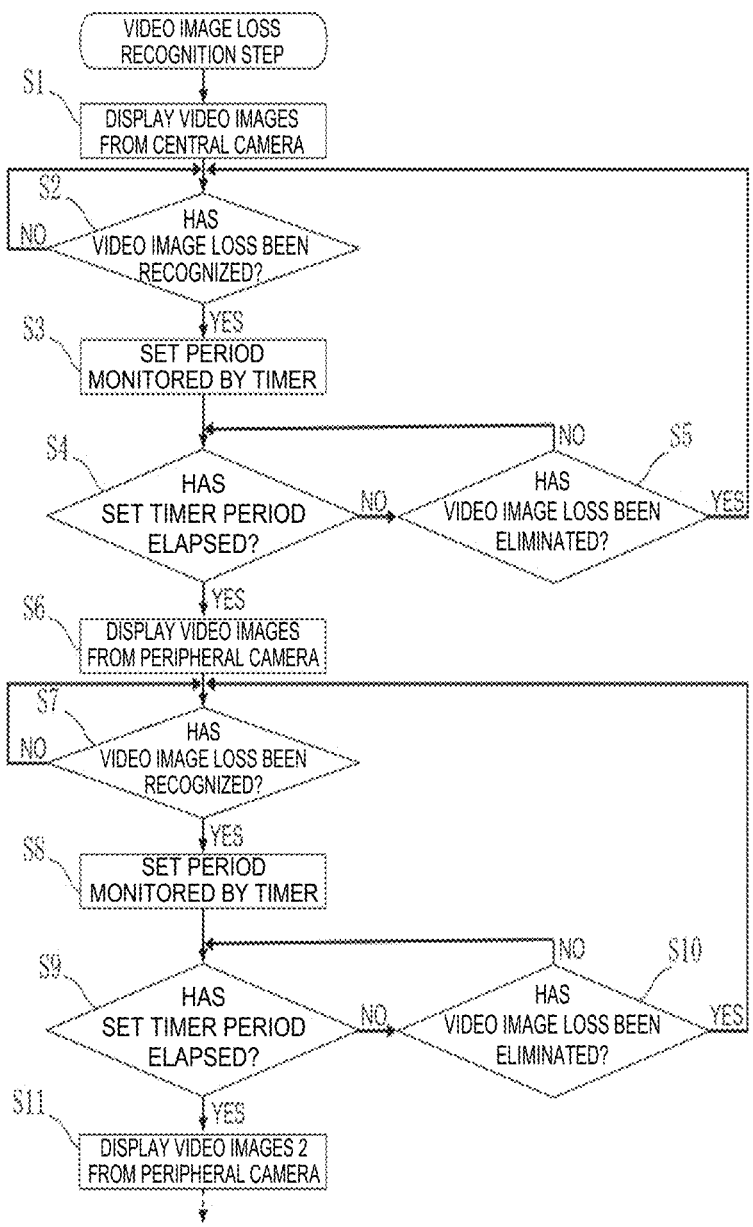

[Figure 20]
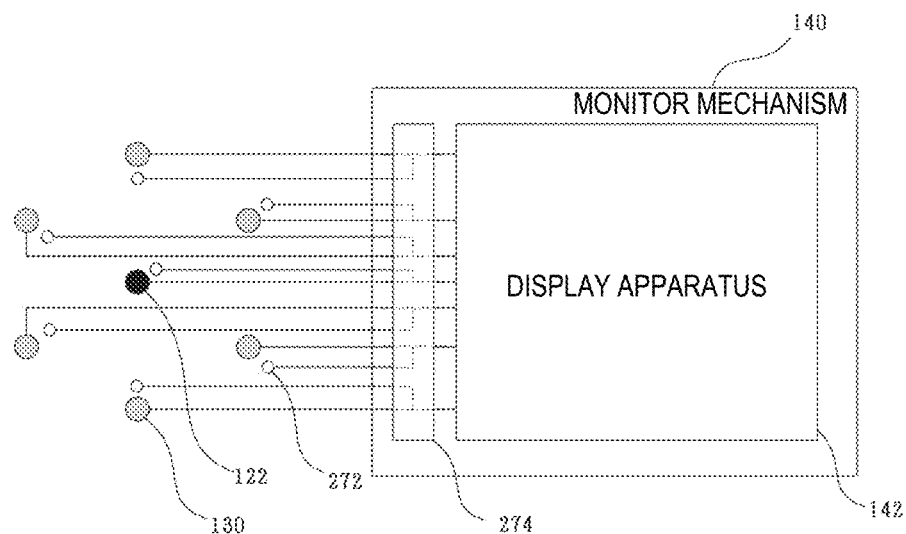
[Figure 21]
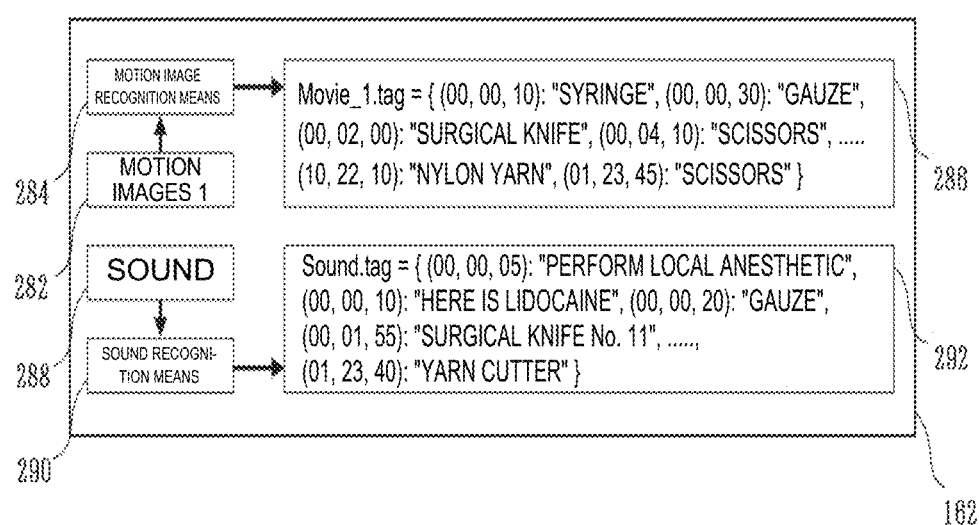

MULTIPLE-VIEWPOINT VIDEO IMAGE VIEWING SYSTEM AND CAMERA SYSTEM

TECHNICAL FIELD

The present invention relates to a system in which a multi-viewpoint camera captures video images of techniques, such as surgical operation, and video images to be displayed on a monitor display are selected from the captured video images.

BACKGROUND ART

Conventionally, there has already been a proposed viewing-target-centered, pegged viewing interface as an audiovisual interface capable of readily selecting a viewpoint from which a multi-viewpoint video content is viewed along an arbitrary direction (Non Patent Literature 1, for example). The audiovisual interface described above is, however, intended to omnidirectionally view the entire body of a person who performs a sport, a performance, or any other action and is not intended to focus on and omnidirectionally view operation performed by a practitioner's hand. When no obstacle is present between a camera and an imaging target, any selected video images contain the imaging target, and it does not matter which video images are selected as a viewpoint candidate. To capture an image of hand performed operation, for example, in surgical operation, however, the practitioner's head and body are interposed between the camera and the hand and cause a problem that the hand cannot be seen. Such video images have no informational value, and the audiovisual interface for multi-viewpoint video images should not use such video images of a viewpoint as a candidate. When video images having no informational value are selected in the viewpoint selection, another viewpoint needs to be selected again.

Note that, in the present specification, the practitioner means not only a surgeon but the following professions:
"Manufacturers
  furniture upholsterer, cutting tool craftsman, metal carver, charcoal maker, weaving technician, glass product manufacturing worker, ceramic technician, cloisonne artisan, and brick/roof tile manufacturing worker, casting artisan, candle manufacturing worker, die manufacturing worker, and others;
Traditional Crafts
  glass blower, doll maker, metal artisan, bamboo craftsman, swordsmith, waxwork craftsman, and "yuzen" dyeing craftsman, Buddhist altar/fittings craftsman, Japanese Umbrella craftsman, pyrotechnist, craftsman who makes "shodo" materials, Japanese paper craftsman, and cabinet maker, craftsman who makes "hagoita" racquets festooned with cloth applique-like portraits, metal decorator, potter, gargoyle craftsman, Japanese lacquer craftsman, craftsman who makes lantern, Japanese round fan, and folding fan, paper hanger, bow/arrow maker, mask craftsman ("noh" mask, "kyogen-play" mask, and "kagura" mask), lacquer ware artisan, and others;
Architecture/Civil Engineering
  plasterer, carpenter, stonecutter, carpenter specializing in temple, shrine, and other buildings, painter, and sheet metal artisan, tatami craftsman, welder, electrician, landscaper (gardener), and others;
Food-Related Professions
  licensed cook, sushi chef, maker of Japanese sweets, salt maker, tofu maker, baker, and rice wine maker, buckwheat noodle maker, coffee bean roaster, fermented soybean paste maker, soy sauce maker, wine maker, tofu maker, and others;
Service (Fashion, Medical Professions)
  beautician, barber, laundry worker, shoemaker, Japanese dressmaker, aesthetician, total beautician, Japanese kimono dresser, currier, leather dressmaker, bodywork therapist, judo therapist, chiropractor, Japanese massage/finger pressure therapist, practitioner in acupuncture and moxibustion, magician, and others; and,
Arts
  artist painter, calligrapher, and others."

As described above, to view and listen to a multi-viewpoint video content of hand performed operation, such as surgical operation, it is desirable that an audiovisual interface does not use, as a viewpoint candidate, video images that do not show the hand behind an obstacle.

Illumination is used in medical practice, such as surgery, and a shadowless lamp is typically used as a source of the illumination not to produce a shadow of the practitioner's body, particularly the practitioner's head, arm, hand, and other body parts, and surgical instruments on a diseased site under treatment.

In many cases, the shadowless lamp is attached to the front end of an arm suspended from the ceiling and has a structure including a movable, inclinable circular support base, a central lamp disposed at the center of the support base, and a plurality of peripheral lamps disposed around the central lamp and attached to the support base.

During the practice, since a practice assistant who prepares a surgical instrument to be used next and a person who is in a separate room and grasps the progress of the surgery cannot directly view the diseased site under treatment, these persons typically grasp the state of the diseased site under treatment via captured video images.

A camera is used to provide the video images, and the camera is, in many cases, attached to the shadowless lamp because it is convenient to move and incline the camera along with the shadowless lamp. As an example in which a shadowless lamp is provided with a camera, Japanese Patent Application No. 11-267663 (Patent Literature 1) and Japanese Patent Application No. 2016-518657 (Patent Literature 2) have been proposed, in which a camera is provided in a position close to the central light source of the shadowless lamp or in a handle section that allows operation of the shadowless lamp.

In medical practice using a camera-equipped shadowless lamp having the structure described above, the practitioner's body, particularly the practitioner's head, arm, hand, and other body parts, and surgical instruments often hide the diseased site under treatment even when the diseased site is illuminated. The problem will be described in detail below.

CITATION LIST

Patent Literature

[Patent Literature 1]
Japanese Patent Application No. 11-267663
[Patent Literature 2]
Japanese Patent Application No. 2016-518657
[Patent Literature 3]
Japanese Patent Laid-Open No. 2012-120812
Non Patent Literature
[Non Patent Literature 1]
MASE Kenji, TOKAI Shogo, KAWAMOTO Tetsuya, and FUJII Toshiaki, "Study of User Interface Design of Peg Scope Navigation Method for Multi-view Image," Human Interface Society, Research Reports, Vol. 11, No. 1, pp. 7-12, 10-11, March, 2009

When an image of a diseased site under treatment is captured in surgery, action of inspecting the diseased site under treatment by the practitioner, movement of the practitioner's hands and fingers, surgical instruments, or other objects hide the diseased site under treatment, which is the imaging target, resulting in occlusion. To complete the image capture operation without occlusion, it is necessary to adjust the position, direction, and viewing angle of the camera in accordance with the positional relationship between the diseased site under treatment and the practitioner, surgical instruments, or other possible objects that may hinder the image capture operation, all of which keep moving during the surgery. In practice, however, it is difficult to immediately operate the camera in accordance with a change in positions of the diseased site under treatment and the obstacle. Examples of the cause resulting in the difficulty are cited as follows.

A first example of the cause is a difficulty in assigning a person who operates the camera as described above in an actual surgical room. Since the practitioner who is a surgeon and participates the surgery as a primary surgeon or an assistant and an instrument handing nurse who hands a surgical instrument to the practitioner concentrate on the progress of the surgery, it is difficult during the surgery for them to grasp the situation of captured video images. A circumferential nurse who hands an additional surgical instrument to the instrument handing nurse is assigned in the surgical room and operates the camera in the intervals of the task in some cases. It is, however, still difficult for the circumferential nurse to immediately operate the camera whenever the positions of the diseased site under treatment and the obstacle change.

Another example of the cause is the fact that there is a situation in which it is difficult to change the position of the camera. On the surgery site, the diseased site under treatment has been disinfected, the patient who lies on the surgical bed is covered with a sterilized cloth, the practitioner and the instrument handing nurse each wear a sterilized gown over a surgical gown, and instrument stands on which sterilized surgical instruments are put, are placed around the surgical bed. In the operation of capturing images of the diseased site under treatment, it is unacceptable that the camera comes into contact with the sterilized persons and objects, thereby the camera may be disposed only in the vicinity of the position immediately above the diseased site under treatment or a position further away from the sterilized persons and objects. The shadowless lamp is typically disposed in the vicinity of the position immediately above the diseased site under treatment. In the case where the camera is disposed in the vicinity of the position immediately above the diseased site under treatment, since the circumferential nurse who can operate the position of the camera wears no sterilized gown, it is difficult for the circumferential nurse to approach the camera with no contact with the sterilized persons and objects.

The configuration in which a shadowless lamp is provided with only one camera, as in Patent Literatures 1 and 2, could cause a situation in which an obstacle, such as the practitioner's head or hands, is interposed between the camera and the diseased site under treatment, resulting in occlusion, although the diseased site under treatment is illuminated. In this case, to capture images of the diseased site under treatment without the obstacles, it is necessary to manipulate the position of the camera. However, the camera and the shadowless lamp are accommodated in the same enclosure in both Patent Literatures 1 and 2. Therefore, manipulating the position and direction of the camera in accordance with the practitioner's action undesirably changes the position and direction of the shadowless lamp in linkage with the manipulated position and direction of the camera, resulting in a difficulty in illumination of the diseased site under treatment.

In both the cases described above, priority is given to completion of safe surgery over capture of satisfactory video images and to stable illumination of the diseased site under treatment over the operation of the camera in a surgical room. From these reasons, it is difficult for the cameras described in Patent Literatures 1 and 2 to complete capture of images of the diseased site under treatment without occlusion due to an obstacle.

Further, when an obstacle causes occlusion during the recording, the practitioner who concentrates on the progress of the surgery cannot view a display at the same time. It is so difficult for the practitioner to notice that the camera occlusion has occurred that the surgery therefore progresses without recording of the diseased site under treatment.

On the other hand, most necessary information obtained from surgical video images required in an actual medical treatment is contents of medical operation performed on the diseased site under treatment. To allow a viewer who views the captured video images to keep accurately grasping the contents as needed, it is necessary to complete capture of images of the diseased site under treatment without occlusion due, for example, to the practitioner's head, body, arm, and hand.

SUMMARY OF INVENTION

Technical Problem

The present invention has been made in view of the necessities and situations described above, and an object of the present invention is to provide a multi-viewpoint video image viewing system that allows a viewer to view a multi-viewpoint video content and removes in advance video images in which the procedures by hands are hidden as a video image candidate.

Further, another object of the present invention is to provide a camera system that allows completion of operation of capturing images of a diseased site under treatment while allowing a practitioner to concentrate on surgery with no awareness of the image capturing operation and provides high probability of the diseased site under treatment contained in any of the captured video images.

Solution to Problem

A first invention of the present application selects video images to be displayed on a video image display section in advance and presents the selected video images to a viewer by causing an information processing apparatus to perform hand-target image recognition on motion image (video image) data that includes image data captured with a plurality of video cameras and a frame string disposed in a time region to select video images showing a hand or not to select video images showing no hand.

A second invention of the present application relates to a camera unit including a camera and a plurality of light sources. In the camera unit, the illumination range achieved by the light sources falls within the imaging range of the camera, and the camera unit is provided in a plurality of positions to form a shadowless lamp to achieve an arrangement in which the plurality of cameras are distributed in the set of the plurality of light sources that form the shadowless lamp to achieve a situation in which the cameras located in the vicinity of the light sources can complete simultaneous image capture even in a case where the light from any of the light sources impinges on a diseased site under treatment. In this situation, a practitioner does not need to be aware of the image capture situation, and any of the cameras can complete capture of images of the diseased site under treatment with no change in the positions of the cameras but with stable illumination on the diseased site under treatment maintained. Further, even in a case where the shadowless lamp is moved to improve the stable illumination on the diseased site under treatment, any of the cameras can achieve the capture of images of the diseased site under treatment. More specific configurations will be described below.

The second invention of the present application relates, to achieve the object described above, to a camera system including a shadowless-lamp-equipped camera mechanism for capturing video images of a diseased site under treatment in a medical practice, such as surgery, and a monitor mechanism that displays the video images captured by the camera mechanism. The overall form of the shadowless-lamp-equipped camera mechanism is similar to the form of a shadowless lamp typically used in surgery. The shadowless-lamp-equipped camera mechanism includes a plurality of light sources, similar to the typical shadowless lamp, further includes a movable, inclinable overall base and an operation handle which is disposed roughly at the center of the overall base and to which a sterilized cover can be attached, still further includes a central camera unit in a central portion of the overall base and at least one peripheral camera unit around the central camera unit. The overall form and configuration of the shadowless-lamp-equipped camera mechanism is the same as those of a typical shadowless lamp, and the practitioner allows the diseased site under treatment to be illuminated as if the practitioner operated a typical shadowless lamp.

In the shadowless-lamp-equipped camera mechanism, the peripheral camera units each include the plurality of light sources, which include a peripheral camera in the vicinity of the plurality of light sources. The direction of the illumination from the light sources coincides with the imaging direction of the peripheral camera. Therefore, when the illumination from any of the plurality of light sources reaches the diseased site under treatment, the peripheral camera located in the vicinity of the light source emitting light that reaches the diseased site, is likely to capture video images of the diseased site. Conversely, when no illumination reaches the diseased site under treatment, captured video images are unlikely to contain the diseased site. However, since it is difficult to perform the surgery in the situation in which no illumination reaches the diseased site, to grasp the operation handle described above by the practitioner to move and incline the overall base of the shadowless-lamp-equipped camera mechanism so that illumination reaches the diseased site, is the same as operation of a typical shadowless lamp. The operation described above allows restoration of the situation in which an image of the diseased site is captured with the camera in the vicinity of any of the light sources. During the operation, the practitioner does not need to be aware of the image capture situation. Note, that it is essential that the peripheral camera units each include a light source, but whether or not a light source is provided in the central camera unit is arbitrarily determined.

It is desirable that video images from a plurality of cameras are input to the monitor mechanism, and that, at the initial setting, video images displayed on the display apparatus are those from the central camera. However, video images from the peripheral cameras contain a larger amount of information in some cases depending on the situation of the surgery, and the operation apparatus provided in the monitor mechanism can be operated to switch the video images on the display apparatus and simultaneously display a plurality of video images on the display apparatus.

Advantageous Effects of Invention

The first invention of the present application having the configuration described above provides the function of assisting effective viewing of multi-viewpoint video images of techniques, such as surgery. It is expected that removing video images having no informational value, such as video images in which the hand is hidden behind an obstacle and video images that do not contain the hand because the hand does not fall within the viewing angle of the camera, from video image candidates in advance, selecting in advance video images having a large informational value, such as video images containing a large number of hands in the vicinity of the center of the screen, and presenting the selected video images provide an effect of reducing stress felt by the viewer when the viewer selects appropriate video images from a large number of video image candidates.

The second invention of the present application having the configuration described above provides the function of assisting effective use of videos of medical practice, such as surgery.

The practitioner only performs surgery as if the practitioner operated a shadowless lamp in related art without being aware of the image capture, and the capture of images of the diseased site under treatment can be completed.

No special person for the image capture needs to be assigned.

When all cameras are occluded due to an obstacle, the illumination from the light sources does not reach the diseased site under treatment at the same time. The practitioner can therefore notice that visual field loss has occurred and can move and incline the shadowless-lamp-equipped camera mechanism to illuminate the diseased site under treatment resulting in elimination of the visual field loss.

Video images of the diseased site under treatment can be more reliably displayed on a display. A circumferential nurse and an anesthetist involved in surgery, doctors and students who observe the surgery, and managers of the surgical room and other persons involved in the surgery can therefore more accurately grasp the progress of the surgery without having to look from the side facing the back of the practitioner into the actual surgical site, whereby it can be expected that the surgical room is efficiently run and that reduction in contamination reduces the number of surgical site infections.

In addition, as for applications of captured video images of medical treatment including surgery in a medical treatment site, it can be expected to investigate causes of a medical accident, improve the patient's satisfaction by giving the patient a more specific description, improve education of surgeons and young medical persons, and provide other effects.

In the field of dental treatment, Japanese Patent Laid-Open No. 2012-120812 (Patent Literature 3) proposes means for combining a shadowless lamp with a video camera system that outputs multi-viewpoint video images from a plurality of video cameras. However, simply applying the means to medical surgery handling an entire human body cannot achieve satisfactory image capture.

First of all, to capture images of a diseased site under treatment from multiple viewpoints in dental treatment, a plurality of video cameras need to be so disposed that the cameras can capture images of the structure at least down to the molar teeth via the oral slit, which is the entrance of the cavity of the mouth, or the gap between the upper and lower cutting teeth. In the case of an adult male, the oral slit has a size up to about 6 cm, the distance between the upper and lower cutting teeth is up to about 5 cm, and the depth to the third molar tooth is about 6 cm. When a dentist having a dental treatment posture operates a shadowless lamp, the shadowless lamp is located in a position above the patient by 60 to 70 cm at the highest, and thereby the inter-camera distance needs to be smaller than or equal to about 15 cm to capture multi-viewpoint images of the third molar teeth over the distance described above via the oral slit or the gap between the cutting teeth. Of course, when the size of the mouth is small as in the case of a child or a female patient, the cameras need to be disposed in closer positions. In this situation, the cameras are separate from each other only by a distance shorter than the width of the practitioner's head, which may cause occlusion in the surgery of other body parts, and it is difficult to capture images of the diseased site under treatment in the medical surgery. In medical surgery, a body range wider than that in dental treatment is a treatment target, and more persons are involved in the treatment. Therefore, to illuminate the diseased site under treatment satisfactorily, the shadowless lamp needs to include light sources arranged over at least a size slightly greater than 50 cm. Even when the shadowless lamp is provided with a plurality of cameras, no consideration of the positional relationship between the cameras and the light sources causes a situation in which no image of the diseased site under treatment is captured with the cameras although the diseased site under treatment is illuminated, as described above. To allow a person to notice the situation described above, a person who is not directly involved in the surgery needs to monitor the display. To restore the correct situation from the situation in which no image capture is achieved, the position and direction of each of the cameras needs to be manipulated on a shadowless lamp basis. The manipulation prevents the treatment from progressing, possibly resulting in danger to the patient.

BRIEF DESCRIPTION OF DRAWINGS

FIG. 1 shows an example of the configuration of a first invention of the present application.

FIG. 2 is a flowchart showing an example of an algorithm in accordance with which video images are selected in the first invention of the present application.

FIG. 3 is a flowchart showing an example of an algorithm in accordance with which an average point is calculated from hand recognition regions in the first invention of the present application.

FIG. 4 shows an example of recognition regions that are each a region which is recognized by the apparatus according to the first invention of the present application and where a hand region contained in an image has been detected.

FIG. 5 shows an example of the process of detecting hand regions contained in an image, determining a center point of each of the regions, calculating an average point from the average of the coordinates of the center points of the regions, and calculating the distance from the average point to the center point of the image in the apparatus according to the first invention of the present application.

FIG. 6 shows an example of the process of detecting hand regions contained in an image, determining a center point of each of the regions, calculating an average point from the average of the coordinates of the center points of the regions, and calculating the distance from the average point to the center point of the image in the apparatus according to the first invention of the present application.

FIG. 7 shows an example of the process of detecting hand regions contained in an image, determining a center point of each of the regions, calculating an average point from the average of the coordinates of the center points of the regions, and calculating the distance from the average point to the center point of the image in the apparatus according to the first invention of the present application.

FIG. 8 is a schematic view of a camera system according to an embodiment of a second invention of the present application.

FIG. 9 shows a configuration in which an operation apparatus selects video images to be displayed on a display apparatus from video images from a plurality of cameras.

FIG. 10 shows a configuration in which video images from a plurality of cameras are simultaneously recorded by an image recording unit.

FIG. 11 shows an exemplary embodiment in which a plurality of simultaneously captured video images are recorded and simultaneously reproduced by using common captured time.

FIG. 12 shows an exemplary embodiment in which an operation handle is rotated to incline an inclination unit of each peripheral camera unit.

FIG. 13 shows an exemplary embodiment of a guide light irradiating an imaging target, in the case in which the apparatus according to the present invention is provided with a guide light radiator that notifies the direction of video images from a camera.

FIG. 14 shows an exemplary embodiment in which the apparatus according to the present invention includes a microphone.

FIG. 15 shows an exemplary embodiment in which a plurality of video images and sound contents having been simultaneously acquired are recorded and simultaneously reproduced by using common captured time.

FIG. 16 shows an exemplary embodiment in which the apparatus according to the present invention includes a half celestial sphere camera.

FIG. 17 shows an exemplary embodiment of the apparatus according to the present invention in which an operation handle is provided with an apparatus that automatically adjusts a light source, the viewing angle and focusing, and operating the image recording unit and a sound recording apparatus, and a focal distance manipulation apparatus activates the automatic focus adjustment in response to an input from an operation apparatus in a monitor mechanism or inclination of a unit base.

FIG. 18 shows a configuration in which a plurality of recorded video images and sound are cut over the common captured time range and output as a plurality of extracted data sets.

FIG. 19 is a flowchart showing an example of an algorithm in accordance with which video images are switched when the display apparatus recognizes video image loss.

FIG. 20 shows a configuration in which a distance measurement device and a central processing unit provided in the monitor mechanism select video images to be displayed on the display apparatus.

FIG. 21 shows a configuration in which the contents of motion image data and sound data are automatically recognized to create letter string data and letter string tag information is added to captured time information to create list data.

DESCRIPTION OF EMBODIMENT

An embodiment that embodies the first invention of the present application will be described below in detail with reference to the drawings. The drawings are diagrammatically drawn for convenience of the description. The scope of application of the multi-viewpoint video image viewing system according to the embodiment of the present invention is not limited to the configuration shown below and can be applied to an arbitrary configuration.

FIG. 1 shows an example of the present invention in which three video images of a subject 10 captured with three video cameras including one primary camera 12 and two secondary cameras 14 are sent to an image acquisition section 22 in an information processing apparatus 20 and a controller 24 selects one video image, which is sent to a video image display section 34 and then to a display apparatus 40. The number of video cameras is at least two and has no upper limit. The cameras each have a camera ID and simultaneously transmit image data, to which the same time information is added, along with the camera ID information to the image acquisition section 22. Image data sent from the controller 24 to the video image display section 34 at a certain point of time is image data containing hand image data on a hand recognized by an image recognition section 26. The image data containing the hand image data is selected and transmitted by an image (video) selection section 32 from a plurality of image data sets input to the image acquisition section 22. The number of image data sets selected and transmitted by the image (video) selection section 32 is not limited to one, and a plurality of image data sets are selected in some cases. The information processing apparatus 20 and the display apparatus 40 each may be a PC, a smartphone, or a tablet terminal.

FIG. 2 is a flowchart showing an example of an algorithm used by the image (video) selection section 32 in the controller 24. First, the video images captured with the video cameras in temporal synchronization with one another are sent to the image acquisition section 22 in the information processing apparatus 20 and handed over to the controller 24. In this process, the controller 24 receives the handed-over image data, and with respect to each handed-over image data, the image recognition section 26 recognizes recognition regions of an image frame at a certain point of time that are each region where a hand is displayed (step S1, 52, 54, 56, and 58 in FIG. 4). As an example of the image recognition performed by an image capturing apparatus in related art, such as a digital camera and a digital video camera, there has been a proposed method for detecting a human face or hand in an image and tracking the detected face to bring the face into focus or carrying out a predetermined process in accordance with the motion of the detected hand. Examples of the image recognition that can be used as an image recognition technology for videos may include Cloud Video Intelligence provided by Google LLC, Video Indexer provided by Microsoft Corporation, and other application programming interfaces (APIs).

The target of the image recognition for hand recognition may be image data obtained, for example, by using thermography capable of visually displaying a temperature distribution in the form of an image or a depth camera capable of acquiring information on the distance to a subject in the form of an image.

A counter 28 then counts the number of recognition regions in each of the image data sets (step S2). An average point calculation section 30 then calculates the coordinates of an average point from the recognition regions in each of the image data sets (step S3, 70 in FIG. 6). A method for calculating the average point will be described later. Carrying out the steps described above achieves a state in which the number of recognition regions and information on the coordinates of the average point are each imparted to the image data captured at the same point of time by each of the cameras. Based on the state described above, the image (video) selection section 32 first checks the maximum number of recognition regions (step S4). In a case where no hand has been recognized in any of the image data sets, that is, the number of recognition regions is zero in each of the image data sets, primary video images that are video images from the primary camera 12 are selected (step S9) and transmitted to the video image display section 34. Any of the secondary cameras 14 can be redefined as the primary camera 12 and the primary camera 12 can serve as the secondary camera 14 at the same time in accordance with the viewer's operation or a computer algorithm.

In a case where the result of step S4 shows that the maximum number of recognition regions is at least one, image data that maximizes the number of recognition regions is selected (step S5). In this case, it is checked whether a plurality of image data sets have been selected (step S6). In a case where the number of image data sets that maximize the number of recognition regions is only one, video images that include the image data are selected and transmitted to the video image display section 34. In a case where the number of image data sets that maximize the number of recognition regions is at least two, the distance from the coordinates of the average point described above to the coordinates of the center point of the image is calculated in each of the images (90 in FIG. 7), and video images that include image data that minimizes the distance are selected and transmitted to the video image display section 34.

FIG. 3 is a flowchart showing an example of an algorithm in accordance with which the average point calculation section 30 calculates the coordinates of the average point from the recognition regions in each of the image data sets. First, the number of recognition regions obtained by the counter 28 for each of the image data sets is checked (step S31). Image data showing that the number of recognition regions is zero, that is, no hand has been recognized does not undergo the average point calculation (step S36). In a case where the number of recognition regions is at least one, information on the coordinates of the recognition regions detected by the image recognition section 26 is used to calculate the coordinates of the center point of each of the regions (step S32, FIG. 5 shows an example in the case in which each of the regions is recognized as a rectangle. In this case, the center point has coordinates that are the average of the coordinates of the four corners of the rectangle). It is then checked whether the number of recognition regions is at least two (step S33). In the case where the number of recognition regions is one, the center point of the region is the average point of the image captured with the camera (step S35). In the case where the number of recognition regions is at least two, the coordinates of all center points of the recognition regions are averaged, and the averaged coordinates are defined as the coordinates of the average point (step S34, 70 in FIG. 6).

Note that, the algorithms shown in FIGS. 2 and 3 are each an example, and the invention of the present application may encompass any algorithm that allows selection of video images that provide expected results, that is, no selection of video images that allow no hand recognition, selection of video image containing many hands or video images that allow hand arrangement to surround the center of the video images, even when the steps are swapped in terms of order or a step is added or deleted.

The controller 24 does not need to carry out the processes from image recognition to video image selection on the image data in all the frames of the video images sent to the image acquisition section 22 and may perform the processes intermittently. The time interval at which the processes are carried out can be adjusted in accordance with the viewer's selection or a computer algorithm, such as every 5 or 10 seconds.

FIG. 4 shows an example of recognition regions 52, 54, 56, and 58, which are each a region where a hand has been recognized by the image recognition section 26. FIG. 4 shows a case where the recognition regions are each a rectangle, and the recognition regions may each instead have an elliptical shape, a polygonal shape, or any other mechanically recognizable shape. The rectangles are drawn on the screen for clarity but are not necessarily displayed on the display apparatus described above as an actual user interface and only need to be internally processed in a computer. When the imaging target is surgery, for example, a hand is the target of treatment in some cases. In this case, it is not desirable that a recognition region contains the hand under treatment. Therefore, image recognition means capable of distinguishing a hand covered with a glove and a hand covered with no glove from each other and recognizing each of the hands can be employed.

FIG. 5 shows an example in which the average point calculation section 30 has determined center points 62, 64, 66, and 68 of the recognition regions 52, 54, 56, and 58. When the recognition regions 52, 54, 56, and 58 are each a rectangle, the center points 62, 64, 66, and 68 are each determined by averaging the coordinates of the four corners of the rectangle in some cases or by determining the intersection of the diagonals of the rectangle in other cases. There are still many other methods for determining the center point of a rectangle, and any method for eventually calculating a point that is identical or approximates to the center point may be employed. In a case where the recognition regions are not each a rectangle, a method for calculating the area of each of the recognition regions and determining the center of gravity of the recognition region as the center point may be employed.

FIG. 6 shows an example in which the average point calculation section 30 has determined an average point 70 of the center points 62, 64, 66, and 68. The coordinates of the average point 70 may be calculated as the coordinates obtained by calculating the average of the coordinates of the center points 62, 64, 66, and 68 described above.

FIG. 7 shows an example in which the image (video) selection section 32 determines the distance between the average point 70 and the center point 60 of the video images based on the coordinates of the aforementioned average point 70 calculated by the average point calculation section 30 described above. Note that, the distance in FIG. 7 is calculated in consideration of both the coordinates x and y and may instead be calculated, for example, by using one of the coordinate x or y. A distance 90 between the average point 70 and the center point 80 of the video images may be determined by the image (video) selection section 32, as in the configuration described above, or the distance 90 between the average point 70 and the center point 80 of the video images may be calculated in advance by the average point calculation section 30 described above. In the latter case, the distance 90 may be handed over to the image (video) selection section 32 and used to select video images.

An embodiment that embodies the second invention of the present application will next be described below in detail with reference to FIG. 8 and the following figures. The figures are diagrammatically drawn for convenience of the description.

FIG. 8 shows an example of the present invention in which a camera system 110 includes one central camera unit 116 and six peripheral camera units 126. Light sources 124 of the central camera unit do not essentially form a shadowless-lamp light source, and light sources 132 of each of the peripheral camera units may be so disposed as to surround a peripheral camera 130, as shown in the example of FIG. 1, or may be so disposed as to be juxtaposed. A central camera 122 may be so provided as to be adjacent to an operation handle 120, as shown in the example of FIG. 8, or may be provided in the operation handle. Video images from each of the cameras are displayed on a display apparatus 142 of a monitor mechanism 140. The number of shadowless-lamp-equipped camera mechanisms 112 and the number of monitor mechanisms 140 are 1:1 at the minimum and may be a plural number: 1, 1: a plural number, or a plural number: a plural number. The monitor mechanism 140 is fixed to a wall surface of a surgical room in some cases or is movable on a cart in other cases, but not necessarily. There may be a case where the monitor mechanism 140 is installed in a surgical room or a staff room in a medical office via the network in the hospital, or another case where the monitor mechanism 140 may be installed in another facility room under the conditions of the patient's agreement, and the situation of the surgery is viewed as live surgery over the Internet. Video images displayed on the display apparatus 142 can be selected by using an operation apparatus 144. The operation apparatus 144 may be buttons, a mouse, or a keyboard provided on the monitor mechanism 140, a touch panel that forms the display apparatus 142, a remote controller wirelessly connected to the monitor mechanism 140, or the combination thereof. The remote controller placed in a sterilized plastic bag can be used by a person who is involved in the surgery and wears a sterilized gown to select video images. The display apparatus 142 can enlarge part of the displayed video images and display the enlarged video images, and in a case where the diseased site under treatment is small in the video images, the diseased site can be selected, enlarged, and displayed. A region to be enlarged can be selected by displaying a pointer on the display apparatus 142 and manipulating the pointer with a mouse or operating a touch panel that forms the display apparatus 142.

FIG. 9 shows a configuration in which the operation apparatus 144 selects video images to be displayed on the display apparatus 142 from video images from the central camera 122 and the six peripheral cameras 130. On a surgery site, a practitioner does not view video images on the display, but surgical-room nurses and observers who do not participate the surgery primarily view the video images on the display. The present invention provides means for selecting, displaying, and enlarging a plurality of captured video images via the monitor mechanism. The video images from each of the cameras can be so specified display to be turned on or off. In a case where no specification is issued, only video images from the central camera 122 are displayed on the display apparatus 142. The screen of the display apparatus is automatically divided in accordance with the number of cameras specified to be turned on, and video images from the turned-on-cameras are displayed in the respective divided regions. The operation apparatus 144 can be used to adjust the size ratio among the divided regions and the order in accordance with which the video images are arranged. Further, the video image displayed in the divided regions can each be enlarged.

FIG. 10 shows a configuration in which an image recording unit 162 simultaneously inputs video images from the central camera 122 and the six peripheral cameras 130. A switch, that is not shown but operates start and stop of image recording, is provided and the start and stop of image recording performed by all the cameras are controlled by the one switch. The switch provided on the image recording unit, on the operation handle 120 shown in FIG. 1, on the remote control, or the combination thereof may be employed.

FIG. 11 shows an exemplary embodiment in which a plurality of video images simultaneously captured with the central camera 122 and two peripheral cameras 130 are recorded by an image recording apparatus 164 with a common captured time 166 added to the video images, a plurality of motion images including an arbitrary combination of the video images are simultaneously reproduced, via output means 168, with captured time/date signals Sg1 aligned from a captured time signal adding apparatus 166, and the video images are displayed on the display apparatus 142 of the monitor mechanism 140. In the case where the plurality of videos are simultaneously reproduced, to reproduce the same scene in accordance with the actually captured time, it is necessary in related art to perform fine adjustment of the reproducing points of time if the recorded points of time recorded in the videos deviate from each other. To eliminate the necessity described above, the present invention provides means for recording a plurality of video images simultaneously and concurrently with the recorded points of time aligned and means for simultaneously reproducing the plurality of recorded video images or outputting the video images in the form of data with the captured points of time aligned. In the present invention, the plurality of videos are reproduced with the captured time aligned associated with each motion image aligned with those associated with the other videos by using the common captured time signal Sg1, whereby the video images on the screen can be switched to video images from another camera or the video images from a plurality of cameras can be simultaneously displayed with no time discrepancy. Although FIG. 11 diagrammatically shows the two peripheral cameras 130, it is desirable in practice that at least three peripheral cameras 130 surround the central camera 122 for effective image capture that avoids the visual field loss. The image recording unit 162 may be separate from the monitor mechanism 140 in some cases, as shown in FIG. 11, or may be incorporated in the monitor mechanism 140 in other cases. The output means 168 may be provided in the image recording unit 162 in some cases, as shown in FIG. 11, or the operation apparatus 144 may serve as the output means 168 in a situation in which the image recording unit 162 is incorporated in the monitor mechanism 140. In a case where the destination to which the videos are output is the display apparatus 142, as shown in FIG. 11, videos to be displayed on the display apparatus 142 can be selected and the configuration of the screen can be adjusted via the operation apparatus 144, as shown in FIG. 2, while the plurality of simultaneously output videos are simultaneously reproduced. There is a possible case where the output destination is not a display but is a recording medium, such as a DVD. In this case, however, arbitrary videos may be selected from the plurality of videos and output as an independent motion image file or output as one motion image file that allows an arbitrary combination of videos to be juxtaposed in an arbitrary arrangement.

FIG. 12 shows an exemplary embodiment in which a link apparatus 182 mechanically links the operation handle 120 to an inclination unit 184 of each of the peripheral camera units 126 and the operation handle 120 is rotated to operate the inclination units 184. The link apparatus 182 may convert the direction of the rotational force by using a bevel wheel and a helical gear that are not shown and mechanically transmit the force to the inclination units 184 in some cases. As shown in FIG. 12, the peripheral camera units 126 each have a circular shape and are rotated around an axis that coincides with the diameter of the circle to incline with respect to the center of the shadowless-lamp-equipped camera mechanism 112. Instead, the peripheral camera units 126 each do not necessarily have a circular shape, and the center or the pivotal point of the inclination may deviate from the center of each of the peripheral camera units 126 as long as the inclination method allows the inclination to be made with respect to the center of the shadowless-lamp-equipped camera mechanism 112. As another exemplary embodiment, the link apparatus 182 may be a motorized apparatus that transmits an electronic signal to activate a motor provided in each of the inclination units 184 thereby achieve the inclination.

FIG. 13 shows an exemplary embodiment of a guide light irradiating an imaging target 190, in the case in which the aforementioned shadowless-lamp-equipped camera mechanism is provided with a guide light radiator that notifies the direction of video images from a camera. The imaging target 190 is irradiated with guide light 192 traveling along the vertical direction of the video images and guide light 194 traveling along the horizontal direction of the video images, whereby a practitioner can operate the shadowless-lamp-equipped camera mechanism to adjust the inclination along which the imaging target 190 is displayed in video images while viewing the two types of guide light without checking the video images on the display. The two types of guide light are each the combination of linear light fluxes, and a pointer representing a specific direction of the video images should be displayed in one direction. In the present example, the arrow head represents the upward side of the vertical direction (192), but not necessarily, and an arbitrary form can be employed. When the inclination of video images from the plurality of cameras is parallel to the horizontal direction, one guide light radiator suffices, otherwise, the camera units described above may each be provided with the guide light radiator.

The irradiation of the guide light desirably automatically starts when the shadowless-lamp-equipped camera mechanism is moved or inclined, and automatically stops when a fixed period of time elapses. An acceleration sensor is used to sense whether the shadowless-lamp-equipped camera mechanism has been moved or inclined. It is, of course, conceivable not to use an acceleration sensor but to sense occurrence of the movement and inclination with an internal sensor or any other means for measuring the angle of a joint necessary for the movement or inclination of the shadowless-lamp-equipped camera mechanism or the inclination of any of the peripheral camera units.

It is necessary to ensure the safety of a human body, particularly, the eyeballs against the guide light described above.

FIG. 14 shows an example of the present invention in which the shadowless-lamp-equipped camera mechanism 112 is provided with a microphone 202, which outputs sound to a sound recording apparatus 204 and a sound output apparatus 206. In surgery, conversation among persons involved in the surgery is also important information. In particular, in the case of instructing an intern who wears a sterilized gown and participates the surgery, the intern cannot take notes during the surgery, and it is therefore difficult for the intern to accurately memorize instructed contents. Further, the instructed contents are worth being shared also with surgical-room nurses and observers, but the volume of the sound issued from a practitioner may be so small that persons around the practitioner cannot hear the sound in some cases. In FIG. 14, the central camera 122, the monitor mechanism 140, and other components in FIG. 1 are omitted for convenience of the description, and it is noted that the configurations of the omitted components are the same as those in FIG. 1. FIG. 7 shows an example in the case where the microphone 202 is so provided as to be next to the operation handle 120. It is, however, desirable that the microphone 202 is provided in the vicinity of the front end of the operation handle 120, which is close to practitioners, for effective sound collection. Further, since a surgical room is full of sound emitted from a cardiograph, a biological monitor that monitors the blood oxygen saturation, and medical instruments such as an electrosurgical knife, in some cases, it is desirable that the microphone 202 has a noise canceling function and has a unidirectional characteristic along the illumination/imaging direction.

FIG. 15 shows an example of the present invention in which the microphone 202, the sound output apparatus 206, and the sound recording apparatus 204 are added to the configuration shown in FIG. 11. The sound output apparatus 206 may be incorporated in the monitor mechanism 140 as shown in FIG. 15, may be provided independently, or may be an instrument worn by a person involved in the surgery, such as an earphone. It is desirable that the sound recording apparatus 204 is incorporated in the image recording unit 162, as shown in FIG. 15, and records sound with the same captured time 166 at which videos are simultaneously recorded and which is added to the recorded sound. The plurality of videos can be output along with the plurality of sound contents, via the output means 168, with the captured time 166 aligned. Reproducing the plurality of videos and sound contents with the captured time 166 aligned allows the video images on the screen to be switched to video images from another camera and the current video images and video images from another camera to be simultaneously displayed with no time discrepancy.

FIG. 16 shows an example of the present invention in which the central camera 122 of the shadowless-lamp-equipped camera mechanism 112 is a half celestial sphere camera, a stereoscopic camera, or an infrared camera 222 and the camera 222 including any of the cameras described above is provided at the front end of the operation handle 120.

In a surgical room, it is desirable to grasp a wide-range situation, such as not only video images of the diseased site under treatment but persons involved in the surgery and the arrangement and operation of surgical instruments. The present invention provides means for acquiring wide-range video images by using a half celestial sphere camera. In the case where a half celestial sphere camera is used, the central camera unit 116 may be provided with a central camera separately from the half celestial sphere camera in some cases. Also in this case, to obtain video images over 360° with no video image loss, it is desirable to install the half celestial sphere camera at the front end of the operation handle 120. In FIG. 9, in which the monitor mechanism 140 in FIG. 1 is omitted, video images from the half celestial sphere camera 222 are also input to the monitor mechanism 140, as are video images from the other cameras, and the operation apparatus 144 can select video images and adjust a portion of the video images that is the portion to be enlarged.

Further, to grasp the situation of the diseased site under treatment, information obtained from two-dimensionally displayed video images is inferior to information obtained from three-dimensionally displayed video images. The present invention provides means for three-dimensionally displaying video images from the stereoscopic camera 222. In the case where the stereoscopic camera is used, the operation apparatus 144 described above of the monitor mechanism 140 described above allows selection of whether video images on the display apparatus 142 described above are displayed two-dimensionally or three-dimensionally. The stereoscopic camera may be the combination of arbitrary two of the central camera 122 described above and the peripheral cameras 130 described above, or at least one of the cameras described above itself may be the stereoscopic camera.

There is a case where an infrared camera is often used to evaluate the diseased site under treatment in a surgical room. In this case, the infrared camera placed in a sterilized bag needs to be brought to the vicinity of the diseased site for image capture, which is a cumbersome action. The present invention provides means for displaying video images from the infrared camera without the cumbersome action. In the case where an infrared camera is used, one of the central camera 122 described above and the peripheral cameras 130 described above may be an infrared camera or capable of switching to an infrared camera.

FIG. 17 shows the configuration of an example of the present invention in which switches 234, 236, 242, 246, and 248 are provided on the side surface of the operation handle 120, and operating the switches by a practitioner during the surgery allows switching activation of the functions of automatically adjusting the light source, the viewing angle, and the focusing performed by the cameras and start and stop of the image/sound recording, and the function of automatically adjusting the focusing performed by the cameras can also be activated by sensing the inclination of a unit base (244). In related art, since a person involved in the surgery and wearing a sterilized gown cannot touch and set the cameras or record images or sound, it is difficult to perform the setting and recording when the number of persons in a surgical room is insufficient or everybody in the room is wearing sterilized gown. The present invention provides a camera system in which a typical shadowless lamp includes a handle section to which a sterilized cover is attached and which is provided with means for setting the light source, the viewing angle of each of the cameras, and autofocusing and recording images and sound. A sterilized cover is attached to the operation handle 20 before surgery is performed, so that even a practitioner wearing a sterilized gown can operate the operation handle 20. In this case, the cover is desirably made of a transparent, soft material, such as vinyl and thin plastic, not to hinder the operation of the switches 234, 236, 242, 246, and 248. The switches 234, 236, 242, 246, and 248 needs to be so disposed not as to be accidentally activated when an operator touches the operation handle 120 to move or incline the entire shadowless-lamp-equipped camera mechanism or incline any of the peripheral camera units.

It is desirable that the automatic adjustment function of each of the cameras is automatically activated when the positional relationship between the camera and the diseased site under treatment changes. However, using an acceleration sensor provided in any of the peripheral camera units 26 allows detection of movement and inclination of the shadowless-lamp-equipped camera mechanism 112 and inclination of any of the peripheral camera units 126, which may change the positional relationship between the camera and the diseased site, and it is therefore desirable to use the acceleration sensor. An acceleration sensor is, of course, not necessarily used, and occurrence of the aforementioned types of motion may in some cases be sensed by an internal sensor or any other means for measuring the angle of a joint necessary for the movement or inclination of the shadowless-lamp-equipped camera mechanism 12 or the inclination of any of the peripheral camera units 126.

FIG. 18 shows an example of the present invention in which when a plurality of recoded videos 252 and 254 and sound 256 are output to an external recorder, and when the data is not output over the entire recording period, but the data is output for a limited image capture period from T1 to T2, the data is cut in the form of data on the videos and data on the sound over the same temporal range, the sound is combined with the videos, and the resultant videos combined with the sound is output. In the present invention, since all the motion image data and sound data share the same captured time data, a plurality of motion image data sets can be extracted together by specifying the data cutting temporal range from T1 to T2, as shown in FIGS. 4 and 8.

FIG. 19 is a flowchart showing an example of an algorithm in accordance with which video images are switched when the display apparatus described above recognizes video image loss. In a case everybody in a surgical room is wearing sterilized gown and cannot operates the monitor mechanism, it is difficult to switch the video images displayed on the display, causing inconvenience to a surgery assistant or an instrument handing nurse who desires to switch the video image. The present invention provides a camera system in which the monitor mechanism senses that the displayed video images do not include the diseased site under treatment due to disturbances and automatically switches the current video images to other video images. When no video images are specified, the display apparatus displays video images from the central camera (step S1), as described with reference to FIG. 2. The display apparatus can sense that displayed video images are highly likely not to contain the diseased site based on the configuration of the pixels of the video images and automatically switch the video images to video images from another camera. In surgery, the pixels of video images of a diseased site largely show flesh color, red, and the like whereas the pixels of video images displayed when the diseased site is not captured show blue or green, which is a typical color of a sterilized cloth that covers the surroundings of the diseased site or a surgical gown and hat, or green that is the color of a practitioner's gloves. The display apparatus recognizes that a disturbance has occurred when the blue or green pixels occupy a certain proportion of the video images (step S2). In a case where the result of step S2 is YES, a period monitored by a timer is set (step S3). Until the set timer period elapses, the display apparatus keeps recognizing whether the disturbance continues (step S4). When the disturbance is not present anymore, the result of step S5 is YES, and the display apparatus keeps displaying the video images from the central camera. When the disturbance continues, the result of step S5 is NO, and the display apparatus keeps monitoring the disturbance until the set timer period elapses. When the set timer period elapses with the disturbance remaining, the result of step S4 is YES, and the video images are automatically switched to video images from another camera, and the switched video images are displayed (step S6). Thereafter, when disturbance is similarly sensed in the displayed video images, the video images can be switched automatically to video images from another camera. In a case where a plurality of video images is simultaneously displayed, the recognition of the disturbance is performed simultaneously on all the video images. Video images that are not displayed can also be similarly monitored in the background in terms of the disturbance, whereby video images having no disturbance can be specified as video images of switching destination.

FIG. 20 shows an exemplary configuration of the present invention in which a distance measurement device 272 is provided in the vicinity of each of the central camera 122 and the peripheral cameras 130 and a CPU 274 provided in the monitor mechanism 140 automatically selects video images to be displayed on the display apparatus 142. The distance measurement devices 272, when they are each a laser distance meter, each use a light source that complies with the laser class 1 (near infrared) standard and need to ensure the safety of a human body, particularly, the eyeballs. The values measured with the distance measurement devices 172 are transmitted to the CPU 274, and the CPU 274 can control video images from the cameras 122 and 130 located in the vicinities of the distance measurement devices 274 based on the values measured when images of the diseased site under treatment are being captured, in such a way that the video images are not displayed on the display apparatus 42 when the values greatly change over a fixed period.

FIG. 21 shows a configuration of the present invention in which motion image recognition means 284 and sound recognition means 290 automatically recognize the contents of motion data 282 and sound data 288, respectively, to create letter string data and add letter string tag information to the captured time information to create list data 286 and 292. Recorded videos are long-period images and have monotonous color tone and configuration as a whole in many cases, and it is therefore often difficult to identify a recording period of a surgery scene that is desired to be reproduced. As means for eliminating the difficulty described above, there is a method for allowing a viewer of the video to manually add tag information to the motion images, but the method is labor intensive. The present invention provides means for allowing mechanically performing automatic recognition of recorded video images and sound and adding letter string tag information to time information in the image/sound data to allow search for information on the recorded time, thereby identifying a scene desired to be reproduced. Specific examples of the motion image recognition means 284 and the sound recognition means 290 may include Cloud Video Intelligence and Cloud Speech application programming interface (API) provided by Google LLC. In practice, however, since the motion image data 182 and the sound data 188 contain patient information, using the API, which requires connection to a server in Google LLC, requires permission from the patient in advance. To implement the present invention without use of any network outside the facility, the motion image recognition means 284 and the sound recognition means 290 need to be established in the facility before implementation of the present invention.

REFERENCE SIGNS LIST

10 Subject
12 Primary camera
14 Secondary camera
20 Information processing apparatus
22 Image acquisition section
24 Controller
26 Image recognition section
28 Counter
30 Average point calculation section
32 Video image selection section (image selection section)
34 Video image display section
40 Display apparatus
52, 54, 56, 58 Region where hand has been recognized (recognition region)
62, 64, 66, 68 Center point of recognition region
70 Average point of center points of recognition regions
80 Center point of video images
90 Distance between average point and center point of video images

The invention claimed is:

1. A camera system comprising: a shadowless-lamp-equipped camera mechanism that is used in surgery or any other medical practice and is capable of capturing a fixed image and motion images of a diseased site under treatment and/or a practitioner's hand; and a monitor mechanism that displays video images captured by the camera mechanism, wherein the camera mechanism includes
a movable, inclinable base,
at least two camera units disposed in the base, and
an operation handle capable of moving and inclining the entire camera mechanism,
the at least two camera units each include a unit base and at least one camera provided in the unit base,
the camera of the at least two camera units is configured to be capable of simultaneously capturing a fixed image and motion images of the diseased site under treatment and/or the practitioner's hand from different viewpoints, and
the camera mechanism further includes a video image selection switch for switching video images displayed on the display apparatus to video images selected from video images each captured with the camera of the at least two camera units,
wherein one of the at least two camera units is a central camera unit disposed at a center of the base, and the others are peripheral camera units disposed on the base and around the central camera unit,
and the central camera unit includes a central unit base, an operation handle that stands from a central portion of the central unit base and is capable of moving and inclining the entire camera mechanism when operated by the practitioner, and a central camera so disposed as to be built in or adjacent to the operation handle,
and the peripheral camera units each include a peripheral unit base, a peripheral camera disposed on the peripheral unit base, and a plurality of light sources so disposed on the peripheral unit base as to be adjacent to the peripheral camera,
the central camera and the peripheral camera are each configured to be capable of simultaneously capturing a fixed image and motion images of the diseased site under treatment and/or the practitioner's hand from different viewpoints, and
the monitor mechanism includes at least one display apparatus that normally displays video images from the central camera and an operation apparatus capable of selecting video images to be displayed on the display apparatus also from video images captured with the peripheral cameras in response to a viewer's operation.

2. The camera system according to claim 1, wherein the at least two camera units include a plurality of light sources disposed in a vicinity of the camera, and the plurality of light sources each form a shadowless lamp.

3. The camera system according to claim 1, further comprising an image recording unit that simultaneously and concurrently records each of video images captured by the at least two camera units.

4. The camera system according to claim 3, wherein the image recording unit allows simultaneous reproduction of at least two video images simultaneously captured by the at least two camera units in synchronization with each other in terms of captured point of time.

5. The camera system according to claim 3, wherein the image recording unit allows mechanical automatic recognition of image information on recorded video images, search for recording time information by adding tag information to data time information, and reproduction of the video images and sounds from a point of time corresponding to the recording time information.

6. The camera system according to claim 1, further comprising a microphone that acquires sound information containing conversation during surgery, a sound recording apparatus that records the acquired sound information, and a sound output apparatus that outputs the acquired sound.

7. The camera system according to claim 6, wherein the image recording unit allows simultaneous reproduction of video images captured by the at least two camera units and sound recorded by the microphone in synchronization with each other in terms of capturing and recording points of time.

8. The camera system according to claim 1, wherein the monitor mechanism allows the operation apparatus that selects video images to be displayed on the display apparatus to cut video images captured with any of the camera of the at least two camera units over an arbitrary image capture range, enlarges the cut video images, and displays the enlarged video images on the display.

9. A camera system comprising: a shadowless-lamp-equipped camera mechanism that is used in surgery or any other medical practice and is capable of capturing a fixed image and motion images of a diseased site under treatment and/or a practitioner's hand; and a monitor mechanism that displays video images captured by the camera mechanism, wherein the camera mechanism includes
a movable, inclinable base,
at least two camera units disposed in the base, and
an operation handle capable of moving and inclining the entire camera mechanism,
the at least two camera units each include a unit base and at least one camera provided in the unit base,
the camera of the at least two camera units is configured to be capable of simultaneously capturing a fixed image and motion images of the diseased site under treatment and/or the practitioner's hand from different viewpoints, and the camera mechanism further includes a video image selection switch for switching video images displayed on the display apparatus to video images selected from video images each captured with the camera of the at least two camera units, wherein the at least two camera units further each include an inclination unit that inclines the unit base, wherein the operation handle and the inclination units are linked to each other via a link apparatus, and the operation handle is rotated around an axis of rotation to activate the inclination units via the link apparatus to incline each of the bases of the at least two camera units to allow adjustment of a direction of the camera.

10. A camera system according to claim 9, wherein the camera of the at least two camera units each include a focal length manipulator, and the focal length manipulators each have an automatic focus adjustment function that allows automatic adjustment of focusing in accordance with the imaging target, and when the automatic focus adjustment function is deactivated, the focal length manipulators allow activation of the automatic focus adjustment function for focusing when sensing that the entire camera mechanism has been moved, and then allow automatic deactivation of the automatic focus adjustment function after a fixed period.

11. A camera system according to claim 9, wherein the at least two camera units base include a distance measurement apparatus that is located in a vicinity of the camera of the at least two camera units, optically measures a distance to an imaging target, and transmits distance information to a processor provided in the monitor mechanism, and the processor determines that an image of the imaging target has not been captured when the processor senses that the distance abruptly changes by a large amount and the distance does not return to the measured value for a fixed period and is capable of automatically switching the video images on the display apparatus to video images from another camera.

12. A camera system comprising: a shadowless-lamp-equipped camera mechanism that is used in surgery or any other medical practice and is capable of capturing a fixed image and motion images of a diseased site under treatment and/or a practitioner's hand; and a monitor mechanism that displays video images captured by the camera mechanism, wherein the camera mechanism includes a movable, inclinable base,
at least two camera units disposed in the base, and
an operation handle capable of moving and inclining the entire camera mechanism,
the at least two camera units each include a unit base and at least one camera provided in the unit base,
the camera of the at least two camera units is configured to be capable of simultaneously capturing a fixed image and motion images of the diseased site under treatment and/or the practitioner's hand from different viewpoints, and
the camera mechanism further includes a video image selection switch for switching video images displayed on the display apparatus to video images selected from video images each captured with the camera of the at least two camera units,
wherein the display apparatus is capable of recognizing pixels of video images to sense that displayed video images do not display an imaging target including a diseased site under treatment and/or the practitioner's hand and automatically switching currently displayed video images to other video images when the non-display situation of the imaging target remains for a fixed period.

13. A camera system according to claim 12, wherein the camera of the at least two camera units each include a focal length manipulator, and the focal length manipulators each have an automatic focus adjustment function that allows automatic adjustment of focusing in accordance with the imaging target, and when the automatic focus adjustment function is deactivated, the focal length manipulators allow activation of the automatic focus adjustment function for focusing when sensing that the entire camera mechanism has been moved, and then allow automatic deactivation of the automatic focus adjustment function after a fixed period.

14. A camera system according to claim 12, wherein the at least two camera units base include a distance measurement apparatus that is located in a vicinity of the camera of the at least two camera units, optically measures a distance to an imaging target, and transmits distance information to a processor provided in the monitor mechanism, and the processor determines that an image of the imaging target has not been captured when the processor senses that the distance abruptly changes by a large amount and the distance does not return to the measured value for a fixed period and is capable of automatically switching the video images on the display apparatus to video images from another camera.

* * * * *